United States Patent
Lee et al.

(10) Patent No.: US 9,086,339 B2
(45) Date of Patent: Jul. 21, 2015

(54) ELONGATION TESTER

(71) Applicant: SAMSUNG DISPLAY CO., LTD., Yongin, Gyeonggi-Do (KR)

(72) Inventors: In-Nam Lee, Yongin (KR); Sung-Ku Kang, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 64 days.

(21) Appl. No.: 14/077,257

(22) Filed: Nov. 12, 2013

(65) Prior Publication Data
US 2014/0139252 A1    May 22, 2014

(30) Foreign Application Priority Data

Nov. 20, 2012    (KR) .................. 10-2012-0131393

(51) Int. Cl.
| | |
|---|---|
| *G01R 31/00* | (2006.01) |
| *G01N 3/08* | (2006.01) |
| *G01R 31/28* | (2006.01) |
| *G01N 3/32* | (2006.01) |

(52) U.S. Cl.
CPC .............. *G01N 3/08* (2013.01); *G01R 31/2893* (2013.01); *G01N 3/32* (2013.01); *G01N 2203/0282* (2013.01); *G01N 2203/0617* (2013.01); *G01R 31/2886* (2013.01)

(58) Field of Classification Search
CPC ............. G01N 3/00; G01N 3/08; G01N 3/32; G01N 2203/0017; G01N 2203/0282; G01N 2203/0075; G01N 2203/0252; G01N 2203/0254; G01R 1/07378; G01R 1/00; G01R 1/04; G01R 31/2893; G01R 31/2886; G01R 31/2889; G01R 31/2887; B32B 2307/51; B32B 2038/008; G01B 5/30; G01B 7/16; G01L 1/2206; G01L 5/045; H01L 31/03926; H01L 41/0986
USPC ................... 324/513, 515, 660, 691, 756.01, 324/756.07, 756.02, 755.11; 160/328–329, 160/354, 378; 140/108; 227/12–13; 254/10.5, 216; 73/796, 826, 811, 830, 73/862.07, 862.392, 862.471, 862.42
See application file for complete search history.

(56) References Cited

U.S. PATENT DOCUMENTS

| | | | | |
|---|---|---|---|---|
| 2,756,590 | A | * | 7/1956 | Gehman et al. ................ 73/792 |
| 3,958,455 | A | * | 5/1976 | Russell ..................... 73/862.68 |
| 5,600,895 | A | * | 2/1997 | Meyer et al. ................... 33/789 |
| 5,712,430 | A | * | 1/1998 | Meyer ............................ 73/831 |
| 5,819,428 | A | * | 10/1998 | Meyer ........................... 33/787 |
| 6,323,389 | B1 | * | 11/2001 | Thomas et al. ............... 604/370 |
| 6,487,902 | B1 | * | 12/2002 | Ghosh ............................ 73/159 |
| 6,612,189 | B1 | * | 9/2003 | Miyauchi ................. 73/862.392 |
| 6,688,185 | B2 | * | 2/2004 | Knox et al. .............. 73/862.045 |

(Continued)

FOREIGN PATENT DOCUMENTS

| | | |
|---|---|---|
| KR | 10-2007-0121680 A | 12/2007 |
| KR | 10-2012-0030309 A | 3/2012 |

*Primary Examiner* — Patrick Assouad
*Assistant Examiner* — Sean Curtis
(74) *Attorney, Agent, or Firm* — Lee & Morse, P.C.

(57) ABSTRACT

An elongation tester includes a fixed holder configured to hold an end of a tested material, a variable holder configured to hold a side of the tested material, the variable holder being formed of an elastic material and having a holding region that deforms in a longitudinal direction of the side of the tested material in accordance with deformation of the tested material, and a driver configured to reciprocate the fixed holder.

11 Claims, 2 Drawing Sheets

(56) References Cited

U.S. PATENT DOCUMENTS

| | | | |
|---|---|---|---|
| 6,835,461 B1* | 12/2004 | Yamagata et al. | 428/847.2 |
| 7,677,110 B2* | 3/2010 | Perez Blanco et al. | 73/826 |
| 8,097,926 B2 | 1/2012 | De Graff et al. | |
| 8,120,729 B2* | 2/2012 | Choi et al. | 349/96 |
| 8,137,344 B2* | 3/2012 | Jia et al. | 606/45 |
| 2004/0258887 A1* | 12/2004 | Maciag et al. | 428/156 |
| 2004/0261639 A1* | 12/2004 | Vaughn et al. | 101/248 |
| 2005/0073071 A1* | 4/2005 | Yamazaki et al. | 264/216 |
| 2005/0133151 A1* | 6/2005 | Maldonado Pacheco et al. | 156/164 |
| 2006/0147685 A1* | 7/2006 | Potnis et al. | 428/212 |
| 2006/0147716 A1* | 7/2006 | Braverman et al. | 428/411.1 |
| 2006/0148354 A1* | 7/2006 | Shelley et al. | 442/182 |
| 2009/0020913 A1* | 1/2009 | Sakamaki | 264/291 |
| 2011/0234213 A1* | 9/2011 | Stritzke et al. | 324/238 |
| 2012/0070615 A1* | 3/2012 | Shi et al. | 428/143 |
| 2012/0312585 A1* | 12/2012 | Baek et al. | 174/254 |
| 2014/0127485 A1* | 5/2014 | Uto et al. | 428/212 |

* cited by examiner

ELONGATION TESTER

CROSS-REFERENCE TO RELATED APPLICATION

This application claims priority to and the benefit of Korean Patent Application No. 10-2012-0131393, entitled "Elongation Tester" and filed on Nov. 20, 2012, in the Korean Intellectual Property Office, the entire contents of which are incorporated herein by reference in their entirety.

BACKGROUND

1. Field

Embodiments relate to an elongation tester.

2. Description of the Related Art

A flexible substrate and electrode material that may be freely bent may be used for a flexible display. Due to repeated deformation, the electric characteristic of an electrode may be changed so that the performance of the electrode may be deteriorated.

SUMMARY

An embodiment is directed to an elongation tester, including a fixed holder configured to hold an end of a tested material, a variable holder configured to hold a side of the tested material, the variable holder being formed of an elastic material and having a holding region that deforms in a longitudinal direction of the side of the tested material in accordance with deformation of the tested material, and a driver configured to reciprocate the fixed holder.

A wire lead may be inserted into the variable holder in the longitudinal direction of the variable holder.

The wire lead may be longer than the variable holder.

A plurality of variable holders may be provided to surround a perimeter of the tested material.

The elongation tester may further include a supporting unit including a guide rail for guiding a reciprocating motion of one or more of the fixed or variable holders.

At least one of the fixed holder and the variable holder may be supported by the supporting unit.

The driver may be configured to reciprocate the fixed holder in different directions.

The elongation tester may further include a resistance measuring unit configured to measuring a change in resistance of the tested material, and a controller for controlling the driver.

The variable holder may be formed of an elastic polymer material.

The tested material may be a flexible electrode including at least one of a metal nanowire and a carbon nanotube.

First and second fixed holders may hold first and second portions of the tested material, and first and second variable holders may hold third and fourth portions of the tested material, the first and second portions being opposite one another, and the third and fourth portions extending between the first and second portions.

BRIEF DESCRIPTION OF THE DRAWINGS

Features will become apparent to those of skill in the art by describing in detail exemplary embodiments with reference to the attached drawings in which.

DETAILED DESCRIPTION

Figure 1A:
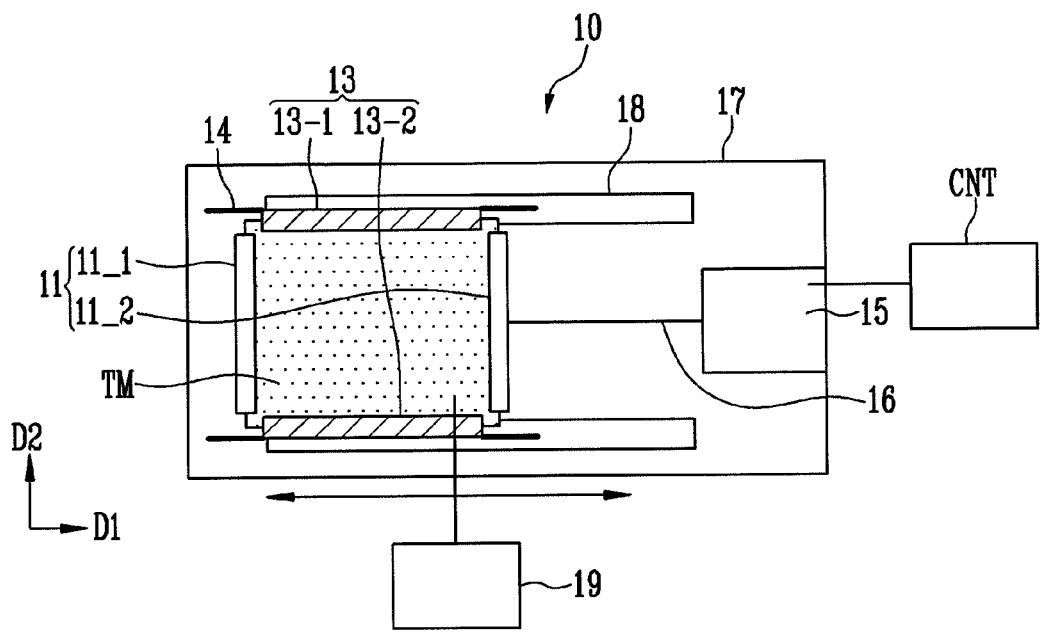
FIGS. 1A and 1B are views schematically illustrating an elongation tester according to an embodiment.
Figure 1B:
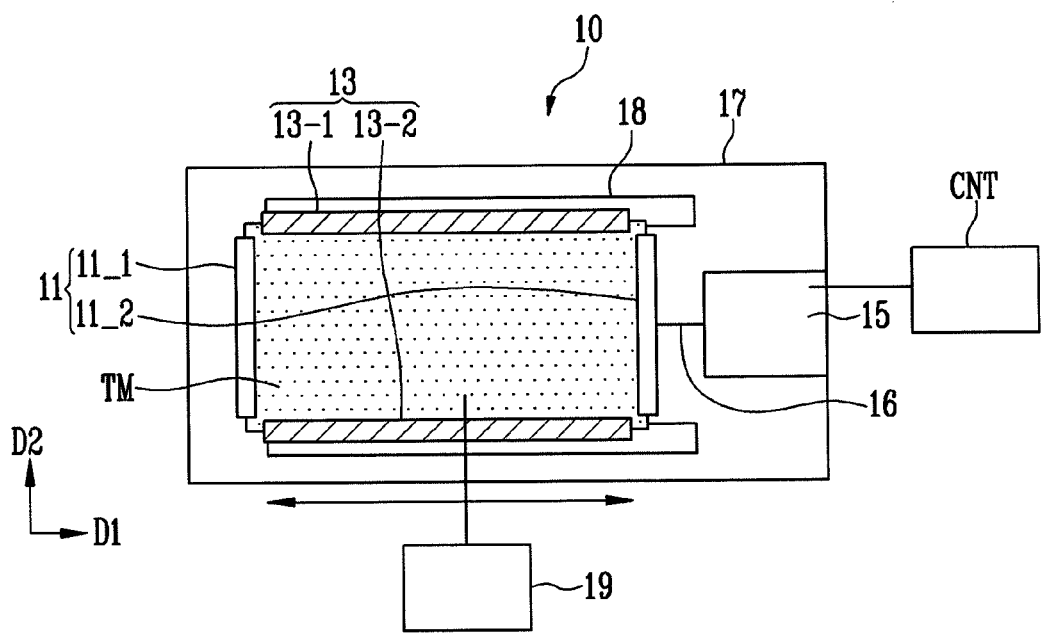

FIGS. 1A and 1B are views schematically illustrating an elongation tester according to an embodiment.

Referring to FIGS. 1A and 1B, an elongation tester 10 according to an embodiment includes a fixed holder 11, a variable holder 13, and a driver 15. In addition, the elongation tester 10 may further include a wire lead 14, a supporting unit 17, and a guide rail 18.

The elongation tester 10 according to the present embodiment expands/contracts a tested material TM in a first direction D1 to test the elongation of the tested material TM.

The tested material TM may be a conductive material having a flexible characteristic and may be, e.g., a touch screen panel or transparent display flexible electrode. The tested material TM may include at least one of a metal nanowire and a carbon nanotube as a composite material in which various materials are mixed.

The tested material TM may be a square that is similar to the shape of a common display panel and that facilitates an elongation test. However, embodiments are not limited to the above, and the tested material TM may have various sizes and shapes in accordance with an elongation direction and the arrangement structure of holders that hold the tested material TM.

The fixed holder 11 holds the end of the tested material TM. In an implementation, a plurality of fixed holders 11 may be provided. The fixed holder 11 may be positioned on one side or at the edge of the tested material TM in the elongation direction.

According to the present embodiment, since the tested material TM is expanded and contracted only in a first direction D1 and is fixed in a second direction D2 perpendicular to the first direction D1, the fixed holder 11 is mounted on the left/right sides of the tested material TM that run parallel with the second direction D2. That is, a first fixed holder 11_1 holds the left side of the tested material TM and a second fixed holder 11_2 holds the right side that faces the left side.

The fixed holder 11 may include, e.g., rectangular compression flat plates oriented in the second direction D2 along one side of the tested material TM, and may have a structure in which the tested material TM is inserted between the compression flat plates that face each other and the compression flat plates are compressed to fix the tested material TM.

In various implementations, the compression flat plates may be combined with each other by, e.g., fastening members (not shown) such as a bolt/a nut, a joint, and/or a clamp to maintain combination strength.

The fixed holder 11 may be formed of metal or plastic having high strength and durability in order to prevent the tested material TM from being deformed and to perform a reciprocating motion tens of thousands of times.

The size, shape, and structure of the fixed holder 11 may be suitably varied. The fixed holder 11 may be attached to and detached from the elongation tester 10 to be exchanged as occasion demands.

The variable holder 13 holds the outside of the tested material TM. The variable holder may be elastically deformable, and may be formed of an elastic material having a holding region that is configured to deform in the longitudinal direction of the outside of the tested material TM in accordance with the deformation of the tested material TM.

According to the present embodiment, since the tested material TM is expanded and contracted only in the first direction D1, the variable holder 13 is mounted on the top/bottom sides of the tested material TM that run parallel with the first direction D1.

For example, a first variable holder 13_1 holds the top side of the tested material TM and a second variable holder 13_2 holds the bottom side that faces the top side.

The variable holder 13 may be a rectangle that extends in the first direction D1 along one side of the tested material TM. The variable holder 13 may be an insertion member having a U section that is shaped to hold the tested material TM.

In addition, the tested material TM may be inserted into the variable holder 13 and the top and bottom flanges of the variable holder 13 may be compressed to fix the tested material TM.

In another embodiment, the variable holder 13 may include compression flat plates like the above-described fixed holder 11.

The variable holder 13 is formed of an elastic material or a ductile material having a holding region deformed in proportion to the deformation of the tested material TM. For example, the variable holder 13 may be formed of an elastic polymer material having high elongation and durability.

The size, shape, and structure of the variable holder 13 may be suitably varied. The variable holder 13 may be attached to and detached from the elongation tester 10 and may be exchanged as occasion demands.

Generally, when the tested material TM is elongated, a part of the tested material that is not provided with a holder to hold the tested material TM may be contracted. Thus, the shape of the tested material TM may be distorted. Such distortion of the shape may not realistically reflect a situation in which the outside of the electrode material is fixed by a frame when the flexible electrode material is actually applied to a product.

The elongation tester 10 according to the present embodiment includes the variable holder 13. The variable holder 13 may entirely hold the outside of the tested material TM without affecting the elongation of the tested material TM, thus more realistically reflecting a situation in which the tested material TM is fixed by a frame.

Since the variable holder 13 is formed of the elastic material or the ductile material having the holding region deformed in proportion to the deformation of the tested material TM, the tested material TM may be easily deformed in the direction perpendicular to the elongation direction as well as in the elongation direction.

The wire lead 14 may be provided in the variable holder 13 in the longitudinal direction to reinforce and prevent the variable holder 13 from being bent in the direction perpendicular to the longitudinal direction. For example, when the elongation of the tested material TM in the first direction D1 is tested in the state where the variable holder 13 is mounted on the top/bottom sides of the tested material TM, the top and bottom sides of the tested material TM are easily extended in the first direction D1 (the elongation direction) by the variable holder 13 but may be prevented from being easily bent in the second direction D2 due to the wire lead 14 inserted into the variable holder 13.

The wire lead 14 is preferably longer than the contracted variable holder 13, considering that the variable holder 13 has a variable length. The length of the wire lead 14 is preferably the same as the length of the maximized (fully extended) variable holder 13 so that the wire lead 14 may cover one side of the tested material TM in the state where the variable holder 13 is deformed by the elongation test.

The driver 15 may drive the fixed holder 11 in a reciprocating motion. The reciprocating motion of the fixed holder 11 (holding the tested material TM) means that the elongation test of the tested material TM is performed.

The driver 15 may be coupled to the fixed holder 11 through a coupling arm 16.

A plurality of drivers 15 may be provided to correspond to the plurality of fixed holders 11. For example, each of the plurality of drivers 15 may be coupled to a fixed holder 11, such that reciprocation in different directions may be achieved. In an implementation, two drivers 15 may reciprocate in opposite directions that run parallel with each other.

When one fixed holder 11 is fixed to the supporting unit 17, the driver 15 may make only the other fixed holder 11 reciprocate. For example, when the first fixed holder 11_1 holds the left side of the tested material TM and the second fixed holder 11_2 holds the right side of the tested material TM, the first fixed holder 11_1 may be fixed to the supporting unit 17 and the driver 15 may drive only the coupled second fixed holder 11_2 to reciprocate in the first direction D1 so that the elongation test may be performed.

The driver 15 may include a motor (not shown) for providing driving power and a gear (not shown) for mechanically transmitting driving power, and may further include various mechanical apparatuses in order to have the fixed holder 11 reciprocate.

A controller CNT may control the driver 15 to control the uniform speed and expansion range of the elongation.

The embodiments are not limited to a particular kind and shape of the driver 15.

The supporting unit 17 may be a frame structure for fixing the elongation tester 10 to the bottom surface, and may support at least one of the fixed holder 11 and the variable holder 13. For example, the fixed holder 11 and/or the variable holder 13 may be installed to move on the supporting unit 17, or may be installed to be fixed and not to move.

The supporting unit 17 may further include a guide rail 18 for guiding the reciprocating motion of the fixed holder 11 and/or the variable holder 13. For example, the fixed holder 11 and the variable holder 13 may be installed in the guide rail 18 that guides the elongation direction. For example, the fixed holder and/or the variable holder may include wheel-shaped structures.

In an implementation, the guide rail 18 may be provided to be adjacent to the top/bottom sides of the tested material TM in the first direction D1. The second fixed holder 11_2 coupled to the driver 15 may precess and recess on the guide rail 18, and the tested material TM may be expanded and contracted to perform elongation.

In an embodiment, the elongation tester 10 may further include a resistance measuring unit 19 for measuring a change in the resistance of the tested material TM and the controller CNT for controller the driver 15.

The resistance measuring unit may measure a resistance change, e.g., a change in electrical resistance, in accordance with the repeated expansion and contraction of the tested material TM. The elongation tester 10 may include various measuring units capable of detecting an electric characteristic value other than the resistance change.

As described above, according to the present embodiment, the variable holder 13 (formed of the elastic material and having the holding region deformed in the longitudinal direction of the outside in accordance with the deformation of the tested material TM) may be provided on the outside of the tested material TM in order to test the elongation while minimizing the distortion of the shape of the tested material TM.

Figure 2:
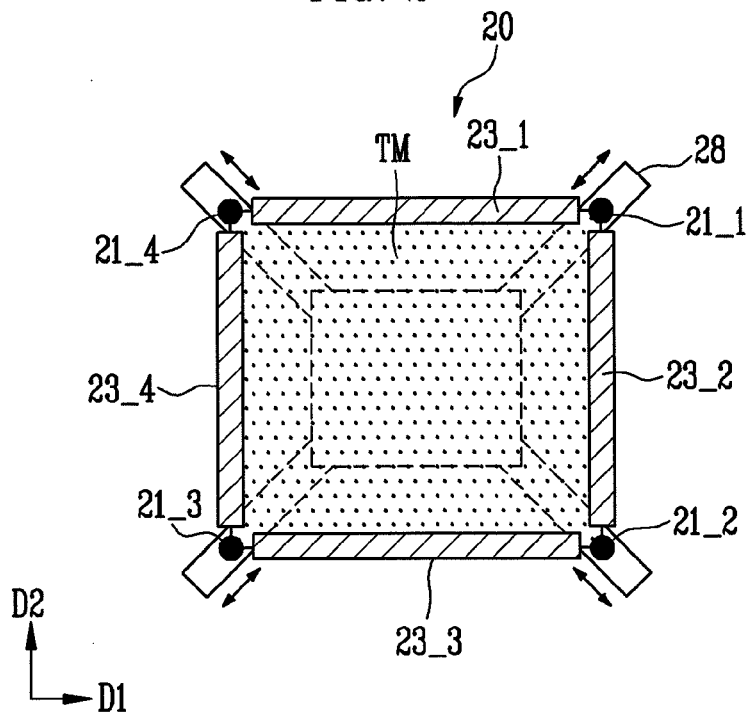
FIGS. 2 and 3 are views schematically illustrating an elongation tester according to another embodiment.
Figure 3:
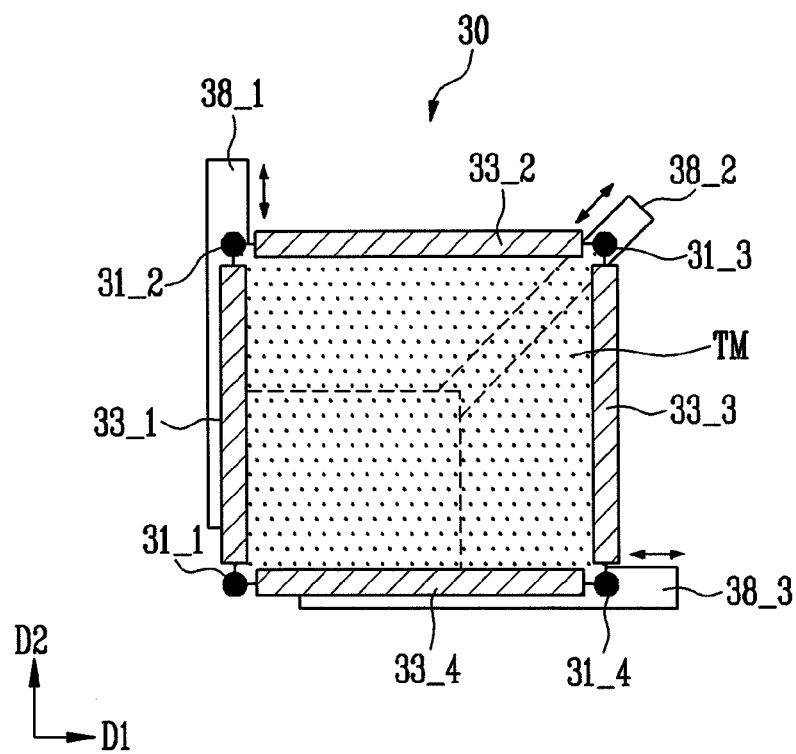

FIGS. 2 and 3 are views schematically illustrating an elongation tester according to another embodiment.

The above-described disclosure may be referred to with respect to the elements denoted by the same reference numerals as those of the above-described elements; redundant descriptions of the elements may be omitted.

Referring to FIG. 2, an elongation tester 20 according to the present embodiment may expand/contract the tested material TM in the first direction D1 and the second direction D2 to test the elongation of the tested material TM.

In the embodiment shown in FIG. 2, four fixed holders 21_1, 21_2, 21_3, and 21_4 are mounted at the four edges or corners of the tested material TM. Four variable holders 23_1, 23_2, 23_3, and 23_4 are mounted on the four sides that form the outside of the tested material TM.

The four fixed holders 21_1, 21_2, 21_3, and 21_4 reciprocate in diagonal directions that form an angle of 45 degrees with the first direction D1 and the second direction D2. The tested material TM may be expanded and contracted in the four diagonal directions to perform elongation. Since the outside of the tested material TM is expanded, the four variable holders 23_1, 23_2, 23_3, and 23_4 are mounted on the four sides that form the outside of the tested material TM.

In the present embodiment, there are no fixed holders fixed to the supporting unit and all of the fixed holders 21_1, 21_2, 21_3, and 21_4 reciprocate.

Although not shown, a plurality of drivers may be provided to correspond to the plurality of fixed holders 21_1, 21_2, 21_3, and 21_4.

Guide rails 28 may be provided to be adjacent to the four edges of the tested material TM in the diagonal directions. The fixed holders 21_1, 21_2, 21_3, and 21_4 may precess and recess on the guide rails 28.

Wire leads, or rods, may be inserted into the variable holders 23_1, 23_2, 23_3, and 23_4 to prevent the variable holders from being bent in the longitudinal direction.

Referring to FIG. 3, an elongation tester 30 according to the present embodiment expands/contracts the tested material TM in the first direction D1, the second direction D2, and a diagonal direction between the first direction D1 and the second direction D2 to test the elongation of the tested material TM.

Here, four fixed holders 31_1, 31_2, 31_3, and 31_4 are mounted at the four edges of the tested material TM. The second, third, and fourth fixed holders 31_2, 31_3, and 31_4 may be configured to reciprocate while the first fixed holder 31_1 fixes an edge of the tested material TM not to move. In an implementation, the second to fourth fixed holders 31_2, 31_3, and 31_4 may be configured to reciprocate in the first direction D1, the second direction D2, and the diagonal direction, respectively.

As described above in connection with previous example embodiments, a pair, or more, of fixed holders may reciprocate on the same axis in opposite directions. However, in the present embodiment, in the state where the first fixed holder 31_1 is fixed, the second to fourth fixed holders radially reciprocate on three different axes in the first direction D1, the second direction D2, and the diagonal direction around the first fixed holder 31_1.

Guide rails 38 may be provided in the three directions to guide the precession and recession of the second to fourth fixed holders 31_2, 31_3, and 31_4.

Although the first fixed holder 31_1 is fixed, since the outside of the tested material TM is expanded, variable holders 33_1, 33_2, 33_3, and 33_4 are mounted on the four sides that form the outside of the tested material TM.

Wire leads may be inserted into the variable holders 33_1, 33_2, 33_3, and 33_4 to prevent the variable holders from being bent in the longitudinal direction as described above.

By way of summation and review, a flexible electrode material may be tested as to elongation in accordance with repeated expansion and contraction of the flexible electrode material. In order to test elongation of the flexible electrode material, a passive method and a nonquantitative method may be used. For example, when the electrode is elongated in a short axis direction, the elongation of the electrode material may simply be measured as to the length to which the electrode may be expanded, without any measures to prevent contraction of the electrode material in the orthogonal axis direction of the elongation direction. When the electrode material is elongated, a part of the electrode material that does not have a holder may contract, so that the shape of the part may be distorted. The distortion of the shape may not realistically reflect the case in which the outside of the electrode material is fixed by a frame when the flexible electrode material is actually applied to a product.

Therefore, in testing the elongation of the flexible electrode material, a method of minimizing unnecessary distortion of the shape of the electrode material without affecting the elongation of the tested material to improve reliability of test is preferred.

As described above, embodiments relate to an elongation tester for grasping a characteristic in accordance with repeated expansion and contraction of a flexible electrode material. Embodiments may provide an elongation tester capable of testing elongation while minimizing distortion of the shape of a tested material. According to the embodiments, a variable holder (formed of an elastic material and having a holding region deformed in the longitudinal direction of the outside of a tested material in accordance with the deformation of the tested material) may be provided on the outside of the tested material, in order to test elongation while minimizing unnecessary distortion of the shape of the tested material without affecting the elongation of the tested material.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An elongation tester, comprising:
   a fixed holder configured to hold an end of a tested material;
   a variable holder configured to hold a side of the tested material, the variable holder being formed of an elastic material and having a holding region that deforms in a longitudinal direction of the side of the tested material in accordance with deformation of the tested material; and
   a driver configured to reciprocate the fixed holder.

2. The elongation tester as claimed in claim 1, wherein a wire lead is inserted into the variable holder in the longitudinal direction of the variable holder.

3. The elongation tester as claimed in claim 2, wherein the wire lead is longer than the variable holder.

4. The elongation tester as claimed in claim 1, wherein a plurality of variable holders is provided to surround a perimeter of the tested material.

5. The elongation tester as claimed in claim 1, further comprising a supporting unit including a guide rail for guiding a reciprocating motion of one or more of the fixed or variable holders.

6. The elongation tester as claimed in claim 5, wherein at least one of the fixed holder and the variable holder is supported by the supporting unit.

7. The elongation tester as claimed in claim 1, wherein the driver is configured to reciprocate the fixed holder in different directions.

8. The elongation tester as claimed in claim 1, further comprising:
   a resistance measuring unit configured to measuring a change in resistance of the tested material; and
   a controller for controlling the driver.

9. The elongation tester as claimed in claim 1, wherein the variable holder is formed of an elastic polymer material.

10. The elongation tester as claimed in claim 1, wherein the tested material is a flexible electrode including at least one of a metal nanowire and a carbon nanotube.

11. The elongation tester as claimed in claim 1, wherein first and second fixed holders hold first and second portions of the tested material, and first and second variable holders hold third and fourth portions of the tested material, the first and second portions being opposite one another, and the third and fourth portions extending between the first and second portions.

* * * * *